(12) United States Patent
Anderson et al.

(10) Patent No.: US 7,563,789 B2
(45) Date of Patent: Jul. 21, 2009

(54) 1-ADAMANTYL CHALCONES FOR THE TREATMENT OF PROLIFERATIVE DISORDERS

(76) Inventors: Gloria Long Anderson, 560 Lynn Valley Rd., SW., Atlanta, GA (US) 30311; Tawfeq Abdul-Raheem Kaimari, 2731 Spindletop La., Kennesaw, GA (US) 30144

( * ) Notice: Subject to any disclaimer, the term of this patent is extended or adjusted under 35 U.S.C. 154(b) by 120 days.

(21) Appl. No.: 11/400,506

(22) Filed: Apr. 7, 2006

(65) Prior Publication Data

US 2006/0189580 A1    Aug. 24, 2006

Related U.S. Application Data

(62) Division of application No. 10/950,875, filed on Sep. 27, 2004, now abandoned, which is a division of application No. 10/224,723, filed on Aug. 20, 2002, now Pat. No. 6,864,264.

(51) Int. Cl.
*C07C 53/128* (2006.01)
*A61K 31/12* (2006.01)

(52) U.S. Cl. .............................. 514/239.5; 514/252.12; 514/315; 514/428; 514/681; 544/106; 544/358; 548/570; 568/306

(58) Field of Classification Search ........................ None
See application file for complete search history.

(56) References Cited

OTHER PUBLICATIONS

Kozlov et al, Russian Journal of General Chemistry (Translation of Zhurnal Obshchei Khimii), 1997, 67(10), pp. 1602-1605.*
Kozlov et al, Zhurnal Obshchei Khimii, 1995, 65(8), pp. 1367-1369.*
Kozlov et al, Seryya Khimichnykh Navuk, 1991, (1), pp. 60-65.*

* cited by examiner

*Primary Examiner*—Zinna N Davis
(74) *Attorney, Agent, or Firm*—James E. Schutz, Esq.; Dean Y. Shahriari; Troutman Sanders LLP

(57) ABSTRACT

The present invention relates to the compounds of the general formula (I), a composition for and a method of treating breast cancer or other proliferative disorders in a subject using a compound of general formula [I],

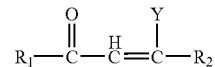

wherein the substituents are as defined in the specification.

6 Claims, 1 Drawing Sheet

1-ADAMANTYL CHALCONES FOR THE TREATMENT OF PROLIFERATIVE DISORDERS

CROSS REFERENCE TO RELATED APPLICATION

This application is a divisional of U.S. patent application Ser. No. 10/950,875 filed on Sep. 27, 2004, now abandoned which is a divisional application of U.S. patent application Ser. No. 10/224,723, filed Aug. 20, 2002, now U.S. Pat. No. 6,864,264 and entitled "1-ADAMANTYL CHALCONES FOR THE TREATMENT OF PROLIFERATIVE DISORDERS," which is incorporated herein by reference.

TECHNICAL FIELD

The present invention pertains to novel 1-adamantyl chalcones, compositions containing the novel 1-adamantyl chalcones, and methods for treating a proliferative disorder using 1-adamantyl chalcones. More particularly, the present invention is directed to a composition for and method of treating breast cancer using 1-adamantyl chalcones, alone or in combination with an additional anti-tumor agent.

BACKGROUND OF THE INVENTION

Cancer is the second leading cause of death in the United States. Half of all men and one-third of all women in the U.S. will develop cancer during their lifetimes.

Cancer is a condition which develops when abnormal cells in an organ begin to grow uncontrollably, replacing normal tissue. This cell proliferation usually forms tumors, although it may also be blood borne. Cancers may behave differently. For instance, breast cancer may grow at a different rate than lung cancer. Although treatment is usually directed to the different characteristics of the particular cancer, most cancer treatment involves chemotherapeutic agents.

Breast cancer is the second leading cause of cancer deaths among women in the United States. Second only to lung cancer; breast cancer is the leading cause of cancer deaths among women aged 40 to 55 years. Breast cancer is the most common malignant neoplasm in women worldwide. The American Cancer Society estimated that in 2001, about 192,200 new cases of invasive breast cancer would be diagnosed among women in the United States. In addition, an estimated 1500 cases would be diagnosed among men. Statistics indicate that in 2001, there were about 40,200 deaths from breast cancer in the United States.

The development of breast cancer has long been speculated to be linked to estrogen stimulation derived from the ovaries. In 1900, Stanley Boyd demonstrated that one-third of the premenopausal women diagnosed with breast cancer benefited from ovarectomies (removal of ovaries). It is now known that the reduction of the estrogen levels that accompany ovarectomy is responsible for this effect, and that any form of endocrine therapy that decreases estrogen levels will benefit approximately one-third of breast cancer patients with pre- or post-menopausal breast cancer.

One of the risk factors associated with increased chance of breast cancer development is genetic pre-disposition. A woman with a first-degree relative with breast cancer is about two to three times more likely to develop breast cancer than a woman with a negative family history. Most of the patients with hereditary breast cancer are thought to have a mutant BRACA1 or BRACA2 gene. In one study of 33 families with evidence of linkage to BRACA1 or BRACA2 gene, the lifetime risk of breast cancer was 87% by age 70.

Breast cancer treatments include surgery, radiation, and chemothereapy. Chemotherapeutic agents and regimens with documented antitumor activity against breast cancer, however, have limited success in treating the disease, as less than one in five patients with stage IV breast cancer are alive five years from the first detection of distant metastases. Although improved response has been observed, overall survival for patients with metastatic breast cancer has not been significantly improved by the progress of the past three decades. Furthermore, despite the proven benefit of adjuvant systemic therapy in reducing the risk of recurrence, a significant fraction of patients with early stage breast cancer still will relapse and ultimately die of metastatic disease. Clearly new active agents and strategies are needed to improve upon this situation.

It is therefore an object of the present invention to provide novel 1-adamantyl compounds for the treatment of breast cancer and other proliferative disorders.

It is a further object of the present invention to provide novel pharmaceutical compositions of 1-adamantyl compounds for the treatment of breast cancer and other proliferative disorders.

It is still another object of the present invention to provide a method for treating tumors from breast cancer and other proliferative disorders by administering to a subject in need of such treatment a therapeutically effective amount of novel 1-adamantyl compounds.

It is yet another object of the present invention to provide a method for treating tumors from breast cancer and other proliferative disorders by administering to a subject in need of such treatment a therapeutically effective amount of novel 1-adamantyl compounds in combination with other anti-tumor agents.

SUMMARY OF THE INVENTION

The present invention relates to the compounds of the general formula (I), a composition for and a method of treating breast cancer or other proliferative disorders in a subject using a compound of general formula,

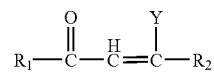

wherein:
R1 is Ad- or Ad--(L1)--, wherein n is 0 or 1, Ad is adamantyl, and L1 is a linking group selected from the group consisting of C1-6 alkylene, C1-6 cycloalkylene, and C1-6 arylene;
R2 is CY1=CHR3, aryl, aryl optionally substituted by X, or HET;
HET is selected from the group consisting of optionally substituted pyrrolidinyl, piperadinyl, morpholinyl, piperazinyl, pyrrolyl, pyridinyl, and pyridazinyl, quinolinyl, and thiophenyl, and wherein the substituent is X;
wherein X is selected from the group consisting of hydrogen, straight chain or branched C1-6 alkyl, halo, amino, C1-6 alkyl amino, C1-6 dialkyl amino, pyrrolidinyl, piperadinyl, morpholinyl, piperazinyl, C1-6 alkoxy, C1-6 aralkoxyl, aryl, C1-6 aralkyl, nitro, cyano and a phosphorus containing group;

Y and Y1 are independently H, C1-6 alkyl, aryl, or halo, with the proviso that when R2 is CY1=CHR3, then Y is hydrogen;

R3 is selected from the group consisting of aryl, aryl optionally substituted by X, or HET;

or a pharmaceutically acceptable salt or derivative thereof.

The compounds of the present invention may also be used alone or in combination with other anti-tumor chemotherapeutic agents for the treatment of breast cancer or other proliferative disorders.

DETAILED DESCRIPTION OF THE INVENTION

Figure 1:
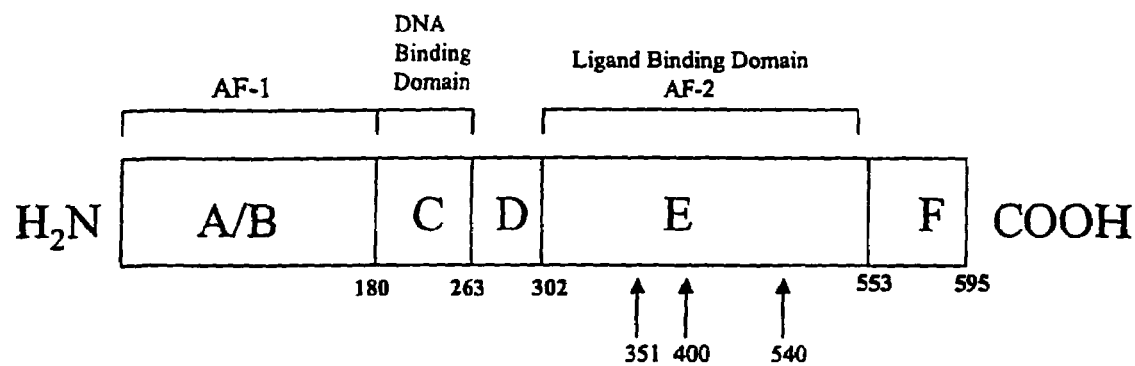
FIG. 1 represents the Human Estrogen Receptor (ER), which was sequenced from MCF-7 human breast cancer cells. The ER protein consists of 595 amino acids and has been separated into six different functional domains.

The following terms shall be used to describe the present invention:

The terms "patient" and "host organism" are used throughout the specification to describe an animal, preferably a human, to whom treatment, including prophylactic treatment, with the compounds and pharmaceutical compositions according to the present invention is provided. For treatment of those infections, conditions or disease states which are specific for a specific animal such as a human patient, the terms patient or host refer to that specific animal. In most applications of the present invention, the patient is a human. Veterinary applications, in certain indications, however, are clearly contemplated by the present invention.

The term "therapeutically effective amount" shall mean the administration of at least one compound according to the present invention in an amount or concentration and for period of time including acute, sub-acute or chronic administration, which is effective within the context of its administration for causing an intended effect or physiological outcome in the treatment of proliferative disorders such as prostate cancer, lung cancer, pancreatic cancer, breast cancer, colon cancer, ovarian cancer, and bladder cancer. Effective amounts of compounds, according to the present invention, include amounts which are therapeutically effective for delaying the onset of, inhibiting or alleviating the effects of the above disease states. Although effective amounts of compounds, according to the present invention, generally fall within the dosage range of about 0.1 mg/patient kg to about 100 mg/patient kg or more, amounts outside of these ranges, in certain instances, may be used, depending upon the final use of the composition.

As used herein, the term "alkyl" is defined as any straight-chained or branched alkyl, including but not limited to methyl, ethyl, propyl, butyl, pentyl, hexyl, isopropyl, isobutyl, sec-butyl, t-butyl, isopentyl, amyl, and t-pentyl.

The terms "proliferative disorder" and "cancer" are used as general terms to describe any of various types of malignant neoplasms, most of which invade surrounding tissues, may metastasize to several sites, and are likely to recur after attempted removal and to cause death of the patient unless adequately treated. As used herein, the term cancer is subsumed under the term tumor or neoplasia. Cancers, which may be treated using one or more compounds according to the present invention, include but are not limited to stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's leukemia, multiple myeloma leukemias, skin melanoma, acute lymphocytic leukemia, acute myelogenous leukemia, small cell lung cancer, choriocarcinoma, rhabdomyosarcoma, neuroblastoma, mouth/pharynx, esophagus, larynx, lymphoma and kidney cancer. Compounds according to the present invention, which are used to treat tumors and/or cancer, are referred to as anti-proliferative.

The term pharmaceutically acceptable salt or derivative is used throughout the specification to describe any pharmaceutically acceptable salt or prodrug form (such as an ester, phosphate ester or salt of an ester or a related group) of an adamantyl compound which, upon administration to a patient, provides directly or indirectly the adamantyl compound or an active metabolite of the adamantyl compound. Pharmaceutically acceptable salt forms of the present compounds are also contemplated by the present invention. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylene-diamine, D-glucosamine, ammonium, tetraethylammonium, or ethylenediamine; or (c) combinations of (a) and (b); e.g., a zinc tannate salt or numerous other acids well known in the pharmaceutical art.

As used herein, the term "HET" represents a mono- or polycyclic heterocyclic or heteroaryl group having ring members selected from carbon, nitrogen, oxygen and sulfur. Representative heterocyclic groups include, but are not limited to pyrrolidyl, piperidyl, piperazinyl, morpholinyl, thiomorpholinyl, aziridinyl, tetrahydrofuranyl and the like. Representative heteroaryl groups include, but are not limited to furanyl, thiophenyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothiophenyl(thianaphthenyl), indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Nonlimiting examples of such partially hydrogenated derivatives are 2,3-dihydrobenzofuranyl, pyrrolinyl, pyrazolinyl, indolinyl, oxazolidinyl, oxazolinyl, oxazepinyl and the like.

The present invention is directed to chalcone derivatives containing an adamantyl moiety and having anti-tumor activity. The compounds are generally represented by the formula

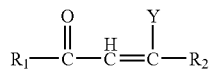

wherein R1 is Ad- or Ad--(L1)--, wherein n is 0 or 1, Ad is adamantyl, and L1 is a linking group selected from the group consisting of C1-6 alkylene, C1-6 cycloalkylene, and C1-6 arylene;
  R2 is CY1=CHR3, aryl, aryl optionally substituted by X, or HET;
  HET is selected from the group consisting of optionally substituted pyrrolidinyl, piperadinyl, morpholinyl, piperazinyl, pyrrolyl, pyridinyl, and pyridazinyl, quinolinyl, and thiophenyl, and wherein the substitutuent is X;
  wherein X is selected from the group consisting of hydrogen, straight chain or branched C1-6 alkyl, halo, amino, C1-6 alkyl amino, C1-6 dialkyl amino, pyrrolidinyl, piperadinyl, morpholinyl, piperazinyl, C1-6 alkoxy, C1-6 aralkoxyl, aryl, C1-6 aralkyl, nitro, cyano and a phosphorus containing group;
  Y and Y1 are independently H, C1-6 alkyl, aryl, or halo, with the proviso that when R2 is CY1=CHR3, then Y is hydrogen;
  R3 is selected from the group consisting of aryl, aryl optionally substituted by X, or HET;

or a pharmaceutically acceptable salt or derivative thereof.

Historical research has focused on the relationship between estrogen and breast cancer. The research has led to an analysis of the estrogen receptor (ER).

Nuclear hormone receptors are a family of hormone-activated transcription factors that initiate or enhance the transcription of genes containing specific hormone response elements. The Human ER, which belongs to this family, was cloned and sequenced from MCF-7 human breast cancer cells. The ER protein consists of 595 amino acids with a molecular weight of 66 kDa and has been separated into six different functional domains, as shown in FIG. 1.

Two of these functional domains are highly conserved in the primary sequence of members of the nuclear hormone receptor superfamily (A/B in FIG. 1). One of the domains (C in FIG. 1, the DNA binding domain (DBD), contains two zinc fingers that mediate receptor binding to hormone response elements in the promoters of hormone-responsive genes. In the C-terminal region, the hormone-binding domain (HBD, E in FIG. 1) contains two regions of sequence homology with other hormone receptors and bestows hormone specificity and selectivity.

The model for estrogen action via the ERα (henceforth referred to as ER) has evolved considerably during the past 40 years. The first realistic conceptual model was proposed by Mueller and colleagues to explain the initiation of metabolic events in the rat uterus by estrogen. Since then, several models have evolved that address the mechanism of how the ER functions in the nucleus and how it activates the transcription of estrogen-responsive genes in the presence of estrogens, an effect differentially blocked by antiestrogens.

The six structural domains of the ER are regions that have been defined based on the putative functions that are contained in each area. The ER contains two areas called AFs: activation functions-1 (AF-1) is located in the amino-terminal region of the ER, and activation functions-2 (AF-2) is located in the carboxyl-terminal region in the ligand binding domain (LBD) of the ER; these are synergistic when the ER is activated by estrogen. AF-1 and AF-2 are autonomous in that they are located at the N- and C-termini, respectively. Activation function-1 (AF-1) is thought to be responsible for the promoter-specific transcriptional activation independent of the presence of ligand and AF-2 provides ligand-specific activation.

The C region contains the DBD and a dimerization domain. The DBD is the most highly conserved region in the nuclear hormone receptor superfamily. The DBD consists of two zinc fingers that fold into two helical domains upon the coordination of one zinc to four cysteines and a third helix that extends from the zinc fingers. These zinc fingers are essential components of the ER because when the ER lacks the DBD, it cannot bind DNA in vitro or in vivo. However, the C region alone is not sufficient to bind an Estrogen Response Element (ERE). The A/B region can be deleted without compromising the DNA binding ability but deletion of the basic amino acids (amino acids 256 to 270) located down-stream of the zinc fingers does impair the ability of the receptor to bind EREs.

There are many similarities in the zinc finger regions among different steroid hormone receptors, but there are precise differences that account for the specificity of each receptor. It is believed that the specificity of a certain receptor is afforded by the first of the two zinc fingers. These conclusions are based on mutagenesis (changes of Cys to Gly) in the region of the first finger. The results prove that the receptor binds to specific nucleic acid residues in the major groove of the DNA helix. The second zinc finger is responsible for stabilizing this interaction through ionic bonds with the phosphate groups in the DNA backbone. In addition to these mutational studies, domain-swapping experiments in which the ER DBD was exchanged with the DBD of the glucocorticoid receptor showed that the chimeric protein activates glucocorticoid responsive genes in the presence of estrogen.

Estrogen diffuses through the plasma membrane of cells where it binds to the ER. For many years, it generally was thought that estrogen bound to the ER in the cytoplasm and translocated into the nucleus, but it is known now that the ER is a nuclear transcription factor that initially interacts with estrogen in the nucleus. Once estrogen binds to the ER, a change in conformation and homodimerization occurs.

Although phosphorylation of steroid hormone receptors enables them to become transcriptionally active, until recently, the role of phosphorylation of the ER was still in question. Phosphorylation of the ER from MCF-7 and calf uterus is estrogen-dependent and, in addition, increases the receptor's affinity for specific DNA sequences. The basal level of ER phosphorylation increases three- to four-fold upon treatment with estrogen and antiestrogens. However, the key to elucidating the mechanism of estrogen action is the identification of the selective sites for phosphorylation. Several serines in the amino-terminal portion of the human ER may play a role in hormone-regulated phosphorylation. However, when phosphopeptide maps of wild-type and mutant ERs treated with estrogen or antiestrogens are compared, the results are similar indicating that differential phosphorylation between these receptors cannot account for any differences in function. An alternate approach might be the identification of enzymes responsible for phosphorylation. There are several protein kinases thought to be involved in phosphorylation of the ER (ER kinase, protein kinase C. protein kinases A, and casein kinase II). Recently, a mitogen-activated protein kinase also was implicated in phosphorylation of the ER on Ser 118 resulting in the activation of ER AF-1. Interestingly, another consequence of phosphorylation of the ER is the regulation of homodimerization through phosphorylation of tyrosine 537.

Although phosphorylation may play a part in receptor activation, exciting progress has been made in understanding how the receptor cooperates with other proteins to assemble a transcription unit for gene activation. The receptor can be viewed as a skeleton to assemble the unit as a prelude to DNA unwinding and the transcription of selected mRNAs. To achieve this, the receptor eventually must interact with other proteins as well as bind to one or several EREs.

As stated above, the ER contains two areas called AFs: AF-1 is located in the amino-terminal region of the ER, and AF-2 is located in the carboxyl-terminal region in the ligand binding domain (LBD) of the ER; these are synergistic when the ER is activated by estrogen. Katzenellenbogen and colleagues used mammalian cells to show that the AF-1 and AF-2 regions, when expressed as separate polypeptides, functionally interact in response to estrogen and antiestrogens. They found that this interaction could activate transcription in response to estrogen. In addition, when mutations were made in AF-1 or AF-2, the functional activity of these domains was inhibited, and no transcriptional activity was seen. Additionally, when mutations were made in the LBD, estrogen binding was eliminated and no transcriptional activity could be detected. These experiments suggested that estrogen binding to the ER facilitates a conformational change that brings AF-1 and AF-2 in direct association with one another leading to synergy that results in transcriptional activation. These experiments provide a mechanistic explanation for the role of the two AFs in mediating hormone-regulated transcription.

In addition to understanding the mechanism through which the ER becomes transcriptionally active, many of the amino acids important in the binding of ligand to the ER have been identified. Harlow and coworkers showed a covalent attachment between Cys530 and both estrogen agonist and an antagonist. This work also suggested that other cysteine residues present in the LBD might be important for ligand-mediated transcriptional activation. Further mutant ERs have been constructed with mutations at the other cysteine residues present in the LBD. Each of these mutants showed an affinity similar to that of the wild-type ER. When these mutants were tested in reporter assays, the mutants C530A and C530S showed unaltered binding to estrogens and antiestrogens, but the transactivation response to both estrogens and antiestrogens had changed. After showing that the C530 is involved in discriminating between ligands, Pakdel and Katzenellenbogen examined the role of amino acids adjacent to the other cysteines in the LBD of the ER. The results showed that the amino-terminal domain of the LBD was important in differential transcriptional activation but not in binding affinity. When the carboxyl-terminal region of the LBD is mutated, this renders the protein transcriptionally inactive although it can still bind ligand, making this a very powerful dominant negative ER. Thus, there is a distinction between the hormone binding and the transactivation functions.

Once the ER has bound estrogen and dimerized, it binds to EREs present in the promoter region of genes. These EREs are 13 base pair palindromic sequences located upstream from the transcriptional start site. The EREs function by enhancing the transcriptional potential of gene. EREs have been identified and defined using reporter systems to test the enhancer ability when exposed to different compounds. Also, deletional analysis has allowed the definition of the sequence of EREs. Optimally, it consists of two inverted repeats separated by any three base pairs. The exact sequence of EREs varies between species and genes.

Some models of estrogen action predict that when the dimerized hormone-receptor complex binds to the palindromic ERE, it forms a looped structure allowing the ER to interact with the transcriptional apparatus at the RNA initiation site. It is thought that the hormone-receptor complex can recruit components of the transcriptional complex and serves as a nucleation site. Previous studies focus on the interaction of the ER with EREs, but more recently, there has been a shift toward the study of ER receptor interactions with ancillary proteins in the nucleus.

Several chemotherapeutic anti-tumor agents are believed to function by the interaction of the ER with EREs or ancillary proteins in the nucleus.

Tamoxifen, a nonsteroidal antiestrogen, is the most commonly used chemotherapeutic agent for treatment of advanced breast cancer and as adjuvant therapy in premenopausal women. Currently, tamoxifen is ubiquitously used in hormone therapy against post menopausal breast cancer. Clinical trials for long term therapy with tamoxifen as a preventive measure against breast cancer have demonstrated its effectivness. Tamoxifen is effective against metastatic breast cancer, delays relapse and has been shown to prolong survival after primary surgery.

Antiestrogens can be classified into two major groups: analogs of tamoxifen or its metabolites, including 4-Hydroxytamoxifen (4-OHT), which have mixed strogenic/antiestrogenic actions in laboratory assays.

The triphenylethlyene structure of tamoxifen has provided the basis for several new analogs that are being investigated in clinics. The finding that tamoxifen is metabolized to 4-Hydroxytamoxifen, a potent antiestrogen, also has provided a central theme for drug development.

Toremifene, or chlorotamoxifen, has been investigated thoroughly as an antiestrogen and antitumor agent in the laboratory, and currently is being used for the treatment of advanced breast cancer and is being tested as an adjuvant therapy. Toremifene is of interest because it does not produce DNA adducts in rat liver and, as a result, is not a potent carcinogen in rat liver.

Idoxifene is a 4-iodopyrrolidino derivative of tamoxifen that has antiestrogenic and antitumor properties in laboratory rats. Idoxifene is a metabolically stable analog of tamoxifen synthesized to avoid toxicity reported with tamoxifen in the rat liver. Substitution of halogens in the 4-position of tamoxifen is known to reduce antiestrogen potency by preventing conversion to 4-OHT, and it was argued that reduced demethylation of the side chain also would avoid the formation of formaldehyde in the liver.

Droloxifene, or 3-hydroxytamoxifen, has been studied extensively as an antiestrogen and an antitumor agent in the laboratory. This drug does not form DNA adducts under laboratory conditions, or produce liver tumors in rats. Extensive clinical testing has shown activity in the treatment of advanced breast cancer in postmenopausal patients.

TAT-59 is a prodrug that is being developed for the treatment of advanced breast cancer. TAT-59 has been shown to inhibit the growth of ER-positive, DMBA-induced rat mammary carcinomas. The drug inhibits the growth of estrogen-stimulated, ER-positive breast cancer cells transplanted into athymic mice. The drug is activated metabolically to a dephosphorylated form that binds with high affinity to the ER. Clinical studies using TAT-59 for the treatment of advanced breast cancer have not been published.

Additionally, compounds are being investigated that do not resemble triphenylethylenes but do exploit the known structural requirements for high binding affinity for the ER.

The compounds LY117018 and raloxifene have high binding affinity for the ER but a lower estrogenic activity than tamoxifen when using rodent uterine assays. They are competitive antagonists of estrogen action but also can block the estrogen-like effects of tamoxifen in the uterus. This demonstrates a single mechanism of action for this class of drugs through the ER.

Although tamoxifen has been used successfully to treat approximately 70% of all ER-positive tumors, there are some disadvantages involved with its use: 1) an increased incidence of endometrial cancer; 2) its mechanism of action almost exclusively lends itself to treatment of ER-positive breast tumors; and 3) with constant treatment of tamoxifen, resistance can develop. Side effects from tamoxifen treatment have been observed in clinical trials. Although it increases hot flashes, it may be beneficial in preventing coronary heart disease because it lowers low-density lipoprotein cholesterol and apolipoprotein B. Not everything under estrogen control is affected by tamoxifen. For example, bone mass and clotting factors remain unchanged. On the other hand, long term treatment with tamoxifen can induce growth of hormone responsive human breast tumor in nude mice. In nude mice with breast tumor and endometrium tumor xenografts, treatment with tamoxifen results in a decrease in size of the breast tumor, but an increase in size of the endometrial tissue. Long term exposure to tamoxifen has no effect on the doubling time of the estrogen receptor negative cell line MDA-MB435, but it induces the formation of a new tetraploid clone that, when implanted in the flank of nude mice yields a greater tumor mass that has a higher mitotic index and is more anaplastic than tumors obtained from wild type MDA-MB435 cells.

Genistein, a natural flavanone compound found in soy, has been proposed to be responsible for the low rate of breast cancer in Asian women. Genistein is a tyrosine kinase inhibitor that works by altering the auto-phosphorylation step on the Epidermal Growth Factor Receptor (EGFR). Genistein is found to exert pronounced antiproliferative effects on both ER-positive and ER-negative human breast carcinoma cells through G2-M arrest, induction of p21Waf1/CIP1 expression, and apotosis.

Genistein also suppresses the production of stress proteins in cells; such as heat shock proteins and glucose-regulated proteins that normally help cancer cells survive destruction by the immune system.

Doxyrubicin is a common chemotherapeutic agent used for treatment of various types of cancers including breast cancer. It is categorized as an anthracycline antibiotic agent that exerts its effect on cancerous and normal cells by binding to the DNA through intercalation between specific bases and blocking the synthesis of new RNA or DNA (or both). This intercalation causes DNA strands scission, and interferes with cell replication.

One of the major problems associated with doxyrubicin treatment is toxicity symptoms such as myelosuppresion, and cardiac toxicity.

Paclitaxel (Taxol®), the prototype taxane, was developed as an anticancer agent at an accelerated pace after the elucidation of its unique mechanism of action and by the initial demonstration of its activity in refractory advanced ovarian carcinoma. The drug functions as a mitotic spindle poison through the enhancement of tubulin polymerization. Multidisciplinary efforts to procure sufficient quantities of this agent have allowed a rapid expansion of clinical trials.

Taxotere is an anticancer agent that inhibits cancer cell division by essentially "freezing" the cells internal skeleton, which is made up of elements called microtubules. These microtubules assemble and disassemble during the cell cycle, but Taxotere promotes the assembly and blocks the disassembly, thus preventing cancer cells from dividing. This action can lead to cancer cell death. The observed side-effect is a reduction of the white blood cell count.

Aredia is used for treatment of patients with osteolytic bone metastases of breast cancer, in conjunction with standard antineoplastic therapy. It exhibits its clinical usefulness by inhibiting bone resorbtion. It is particularly useful for the treatment of hypercalcemia associated with malignancy. It has been proven to reduce the incidence of skeletal complication of metastatic breast cancer. However, the incidence and type of adverse events with Aredia were fatigue, fever, nausea, skeletal pain, transient arthralgias, and myalgias.

Arimidex is used for advanced breast cancer in postmenopausal women whose disease has progressed following therapy with tamoxifen. Many side effects have been reported including asthemia, nausea, hot flashes, pain, and back pain.

Navilbine is a chemotheraputic drug available for the treatment of metastic breast cancer. It is indicated for the treatment of patients with metastatic breast cancer who have failed standard first-line chemotherapy. Side effects include tingling in fingers and toes, constipation, and hair loss.

Chalcone 16 (1,3-Diphenyl-2-propen-1-one) contains aromatic rings (A and C) linked by an olefinic bond and a keto group (B).

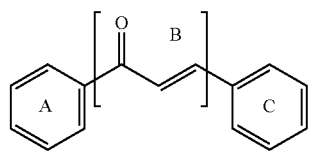

16

Derivatives of Chalcone 16 are widely distributed in higher plants, and play a central role in the biosynthesis of flavonoids. Chalcone 16 itself is considered to be a flavonoid, although its chemical structure is different from that of other flavonoids, which have the 2-phenyl chromone structure 17.

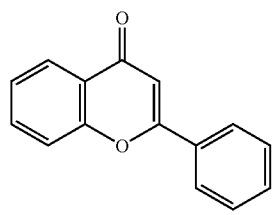

17

Chalcone 16 has a stilbene configuration in which two phenyl groups bracket an α,β-unsaturated carbonyl group. Amongst stilbene derivatives are a variety of synthetic compounds, for example tamoxifen, a widely-used agent for the treatment of breast cancer, which bind to steroid hormone receptors. Compounds containing the α,β-unsaturated moiety (a reactive chemical species) have been found to bind to receptors that increase the activity of phase II enzymes that metabolize xenobiotic.

The similarity between chalcone and tamoxifen is that both exhibit an ene functionality that separates the phenyl groups. It is important for the structure to have this functionality, which is the site for the binding.

The vast majority of derivatives of chalcone 16 have been shown to inhibit lipoxygenase activity and TPA-induced tumor promotion of the mouse epidermis. Isoliquiritigenin 18 (4,2',4'-trihydroxychalcone) is particularly potent in this regard. The biological effects produced by chalcone 16 containing other types of substitutions have also been investigated.

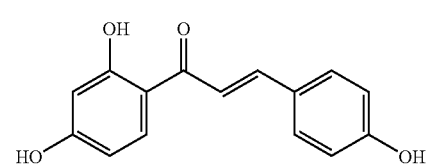

18

In one such study, (E)-4-[3-(3,5-di-tert-butylphenyl)-3-oxo-1-propenyl]benzoic acid 19 was found to induce differentiation of HL-60 leukemia cells and tetratocarcinoma cells.

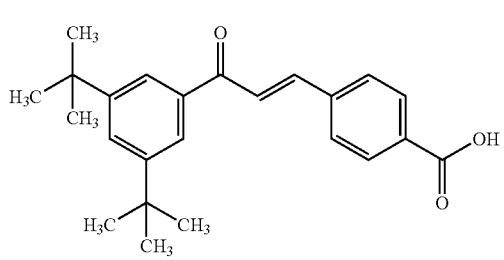

19

In another study, (2E)-1-(2,5-dimethoxyphenyl)-3-[4-(dimethylamino)phenyl]-2-methyl-2-propen-1-one 20 and related compounds were reported to induce antimitotic activity against tumor cells in vitro.

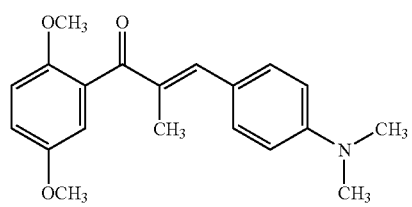

20

Lichochalcone A 21 has been shown to inhibit tumor promotion in mice as well as exhibit antitumor activity against L1210 leukemia and B16 melanoma cells in vivo.

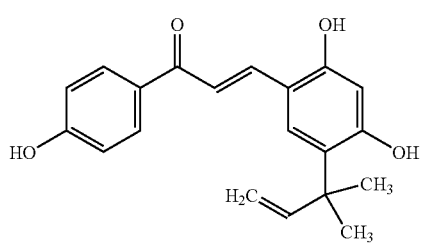

21

More recently, 3'-methyl-3-hydroxychalcone 22 has been reported to be a potent inhibitor of proliferation of several lines of malignant human cells in vitro, and to suppress TPA-induced tumor promoting activity in mouse skin in vivo.

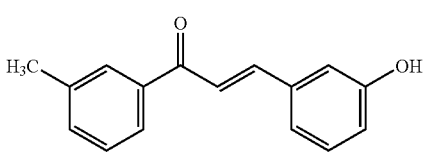

22

An additional attribute of this chalcone 22 is its capacity to inhibit the binding of estradiol to type II estrogen binding sites in HGC-27 cells. Thus, several substituted chalcones have been shown to have effects such as inhibition of cell proliferation and tumor promotion that might endow them with chemopreventive properties.

Retenoids 23, N-phenylbenzamide, which are structurally similar to chalcone, have been shown to exhibit inhibitory activity against non-small cell lung carcinoma (NSCLC).

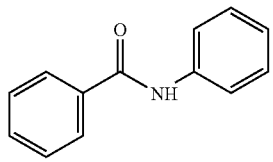

23

Additionally, certain quinoxalines 24 and quinolines 25 show promise as inhibitors of tumor growth.

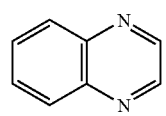

24

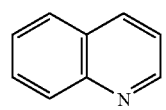

25

Certain derivatives of chalcone 16 and some flavones have shown promise as antitumor agents in breast and other cancers. For example, apigenin 26 and some of its congeners were reported to possess antiproliferative activity against the human breast cancer cell line ZR-75-1.

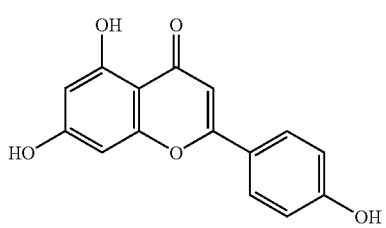

26

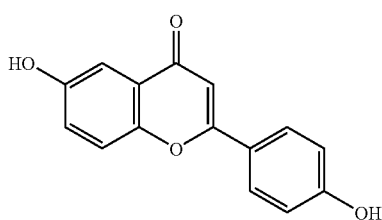

27

6,4'-Dihydroxyflavone 27 has a binding affinity for the ER, and flavone derivative 28 (BE-14348B) exhibits strong estrogenic activity.

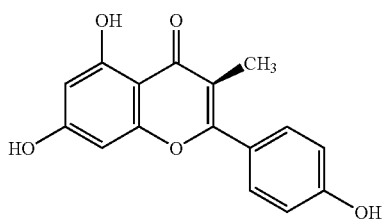

28

The ER binding affinity and the estrogenic activity were also reported for the isoflavone derivative daizein 29.

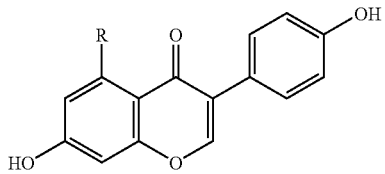

Recently compound (L86-8275) 30 was reported to exhibit antitumor activities against several types of human breast cancer cell lines.

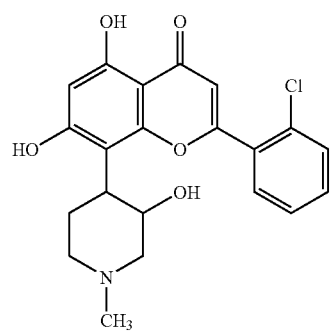

Chalcone 16 is widely consumed by herbivorous animals, and it is not toxic. Derivatives of chalcone 16 seem to have pharmacological properties such as estrogenic activity, inhibition of inflammation and anti-microbe activity, and it has also been reported to have an inhibitory effect on tumor growth.

Many derivatives of adamantane are biologically active compounds with a broad spectrum of activity. The spatial structure, hydrophobicity, and lipophilicity of adamantane ensure favorable conditions for its transport through biological membranes. The introduction of an adamantyl moiety into organic compounds changes and often enhances their biological activities.

A review of the chemical literature revealed that only two compounds containing the adamantane moiety have been reported to exhibit activity against breast cancer. These two compounds are: the acid 6-[3-(1-adamantyl)-4-hydroxyphenyl]-2-2-Naphthalenecarboxylic Acid (CD437, AHPN) 39, and the corresponding disubstituted admantyl ester, 6-[3-(3,5-dimethyl-1-adamantyl)-4-methoxyphenyl]-2-naphthoate 40.

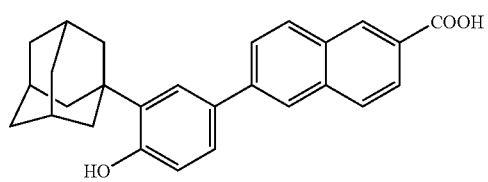

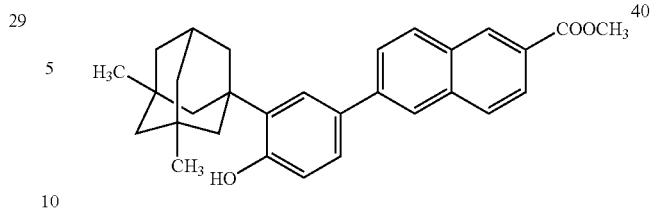

These compounds 39 and 40 have also shown activity against other forms of cancer, especially leukemia.

To our knowledge no study concerning the anti-breast cancer activity of chalcone and chalcone-like derivitives containing the adamantyl moiety has been reported in the current available literature.

The synthetic scheme for the series of adamantyl chalcone and chalcone-like compounds was to prepare derivatives with structural modifications in three regions of the basic chalcone 16 skeleton, (A, B, and C). By altering these basic regions, our laboratory was able to examine some of the substituent effect modifications that modulate biological activity and change potencies of these compounds towards human breast cancer cell lines MCF-7 and MDA-MB435.

Synthesis of the Preferred Embodiments

Preferred compounds of the present invention were conveniently divided into four categories: 1) Series I. Chalcone-like compounds with the aromatic A ring replaced by the adamantane moiety; 2) Series II. Chalcone-like compounds with modification in the A ring and B regions; 3) Series III. Chalcone-like compounds with the aromatic C ring replaced by heterocycle group; and 4) Series IV. Chalcones with the adamantane moiety substituted on the aromatic A ring. The synthesis and characterization of each series will be discussed in the section that follows.

Series I. Synthesis of Chalcone-Like Compounds 43 with Aromatic A Ring Replaced by Adamantane Moiety A series of twelve chalcone-like compounds 43 with aromatic A ring replaced by the adamantane moiety was prepared by base-catalyzed Aldol condensation of 1-adamantyl methyl ketone 41 and substituted benzaldehydes 42 (eq 1).

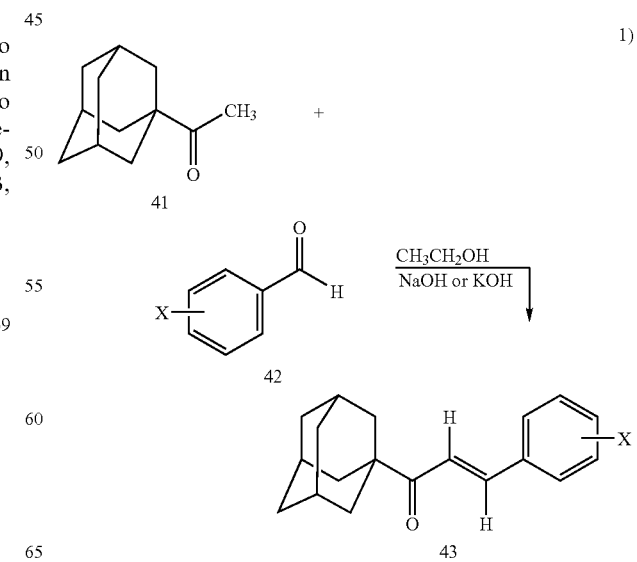

1-Adamantyl methyl ketone 41 reacted readily, at ambient temperature, with a variety of substituted benzaldehydes 42 in alkaline ethanol to afford the corresponding chalcone like compounds 43(a-l) in good yields. Compounds synthesized by this method are shown in Table 1. These compounds were synthesized, purified and fully characterized by NMR, GC-MS, and Elemental Analyses.

Table 1 shows that the percent yield of products tends to be very good to excellent regardless of the substituent on the aromatic ring. The ease with which the compounds were obtained makes this particular reaction a very convenient method for its application in the synthesis of widely varying analogs with potential antineoplastic activity and other biological activities.

Literature reviews and observations in our laboratory suggest that the melting points of adamantane derivatives tend to vary by several degrees according to method of determination (heating rate, sealed capillary, or cover glass). To ensure consistency melting points were determined on a calibrated programmable Electrothermal 9200 Melting Apparatus with set point usually 5° C. below predetermined (estimated) melting point and a ramp rate of 0.3° C./min. This method enabled the accurate determination of melting points within one-tenth of a degree.

TABLE 1

Chalcone-Like Compounds 43 Synthesized with Aromatic A Ring Replaced by the Adamantane Moiety

| Compd | X | % YIELD | MP ° C. |
|---|---|---|---|
| 43a | H | 92 | 90.1-91.4 |
| 43b | p-CN | 96 | 160.1-161.3 |
| 43c | p-NO$_2$ | 68 | 165.0-166.1 |
| 43d | p-Cl | 89 | 141.8-143.3 |
| 43e | p-N(CH$_3$)$_2$ | 92 | 155.1-156.2 |
| 43f | p-CH(CH$_3$)$_2$ | 94 | 93.5-94.9 |
| 43g | p-OCH$_3$ | 96 | 114.3-115.0 |
| 43h | p-F | 94 | 129.8-131.4 |
| 43i | o-Br | 91 | 120.3-121.6 |
| 43j | p-OCH$_2$Ph | 90 | 132.7-134.7 |
| 43k | p-Ph | 86 | 133.6-135.0 |
| 43l | p-Et | 88 | 78.3-79.9 |

Proton NMR data for H$_a$ and H$_b$ (structure 44) were examined to determine trends in chemical shifts as well as to determine the stereochemistry of the double bond. The proton NMR chemical shifts (δ, ppm) and coupling constants (J$_{ab}$, Hz) for H$_a$ and H$_b$ are given in Table 2.

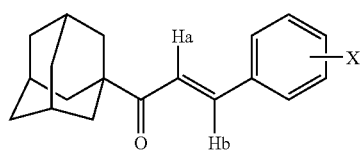

44

Table 2 shows that the chemical shift for H$_b$ varies from 6.98 to 8.08 ppm depending upon substituent X on the aromatic ring. Electron withdrawing groups tend to give signals at lower field (for instance NO$_2$, 7.28; F, 7.64 ppm) whereas electron donating groups show signals at higher field (N(CH$_3$)$_2$ 6.98, CH(CH$_3$)$_2$ 7.15 ppm).

The values for the coupling constants J$_{ab}$ for protons H$_a$ and H$_b$ are consistent with trans stereochemistry. It is widely known that for three-bond proton-proton coupling, the coupling constant J$_{ab}$ depends on the dihedral angle φ between H$_a$ and H$_b$. This dependence of the coupling constant J$_{ab}$ on dihedral angle φ is described by the well known Karplus-Conroy curve. For cis protons H$_a$ and H$_b$ on a double bond in alkenes, the dihedral angle φ is zero degrees (0°). Similarly, for trans protons H$_a$ and H$_b$ on a double bonds in alkenes, the dihedral angle φ is one hundred and eighty degrees (180°). A review of the Karplus-Conroy curve revealed that it predicts larger coupling constants for trans H$_a$ and H$_b$ stereochemistry about a double bond in alkenes. Consistent with the Karplus-Conroy curve prediction, experimental measurements have shown that the coupling constant J$_{ab}$ for cis protons H$_a$ and H$_b$ usually fall within the range of 9-12 Hz, while the coupling constant J$_{ab}$ for trans protons H$_a$ and H$_a$ generally fall within the 14-17 Hz range. The proton coupling constants J$_{ab}$ for H$_a$ and H$_a$ in compounds 43(a-l) vary from 15.4 to 15.9 Hz, all within the range for a trans substituted double bond. Therefore, we have assigned a trans configuration for these compounds.

TABLE 2

Proton NMR Chemical Shifts and Coupling Constants for H$_a$ and H$_b$ (43)

| | | Chemical Shift (ppm) | | Coupling Constant J$_{a-b}$ |
|---|---|---|---|---|
| Compd | X | H$_a$ | H$_b$ | (Hz) |
| 43a | H | 7.69 | 7.18 | 15.6 |
| 43b | p-CN | 7.67 | 7.23 | 15.6 |
| 43c | p-NO$_2$ | 7.68 | 7.28 | 15.7 |
| 43d | p-Cl | 7.62 | 7.14 | 15.6 |
| 43e | p-N(CH$_3$)$_2$ | 7.67 | 6.98 | 15.4 |
| 43f | p-CH(CH$_3$)$_2$ | 7.69 | 7.15 | 15.9 |
| 43g | p-OCH$_3$ | 7.65 | 7.05 | 15.4 |
| 43h | p-F | 7.64 | — | 15.6 |
| 43i | o-Br | 8.08 | 7.12 | 15.7 |
| 43j | p-OCH$_2$Ph | 7.67 | 7.07 | 15.5 |
| 43k | p-Ph | 7.74 | 7.23 | 15.4 |
| 43l | p-Et | 7.67 | 7.18 | 15.5 |

Two compounds in this series 43f and 43g were successfully recrystallized for crystal structure determination. The crystalline structures obtained for these two compounds supported the stereochemical assignment made by the NMR. The conformation of the styrene subunit with respect to the carbonyl for 43f is trans with o1-c1-c2-c3 and c1-c2-c3-c4 torsion angle values of −11.8 and 176.0, respectively. Likewise the conformation of the styrene subunit with respect to the carbonyl for 43g is trans with o1-c1-c2-c3 and c1-c2-c3-c4 torsion angle values of −4.7 and 179.4, respectively.

The fragmentation pattern is very consistent for all these compounds. The base peak observed at m/e 135 (except for the N,N-dimethyl and methoxy derivatives) arises from the decomposition of the adamantyl cation. This fragmentation of adamantane is very common in 1-susbtituted adamantanes. However, the parent peak, if it appears at all, is very weak.

Series II. Chalcone-Like Compounds 45 with Modification in A and B Regions

A series of chalcone-like compounds 45 with modification in the A and B regions was prepared by based-catalyzed Aldol condensation of 1-adamantyl methyl ketone 41, with substituted cinnamaldehydes 44 in alkaline ethanol at ambient temperature to give the corresponding chalcone-like compounds 45 (eq. 3). The percent yield and melting points for these compounds 45 are presented in Table 3.

TAABLE 3

Chalcone-Like Compounds 45 Synthesized with Modification in the A and B Regions

| Compd | X | Y | % YIELD | MP ° C. |
|---|---|---|---|---|
| 45a | OCH₃ | H | 71 | 188.0-190.0 |
| 45b | H | CH₃ | 74 | 158.8-160.3 |
| 45c | H | Cl | 68 | 171.2-172.1 |

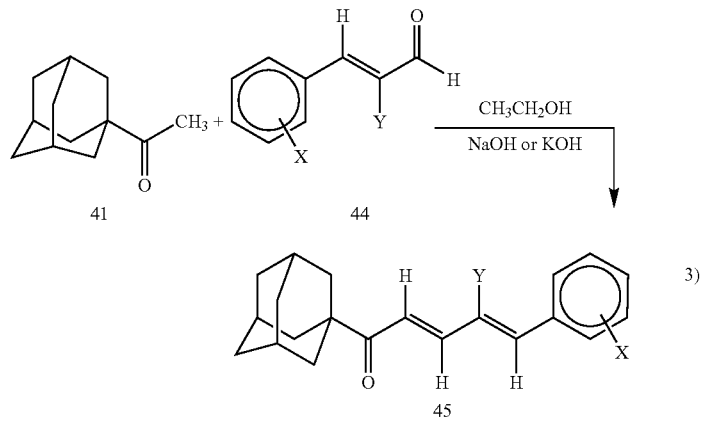

Series III. Chalcone-Like Compounds 47 with Aromatic C Ring Replaced by Heterocycle Group A series of chalcone-like compounds 47 with modification in the A and C ring was synthesized. Het is used to represent the heterocyclic group. The reaction was carried out via aldol condensation of 1-adamantyl methyl ketone 41 and the heterocyclic aldehyde 46 to afford the desire product 47 as shown in (eq 4). The percent yield and melting point for these compounds 47 are presented in Table 4.

TABLE 4

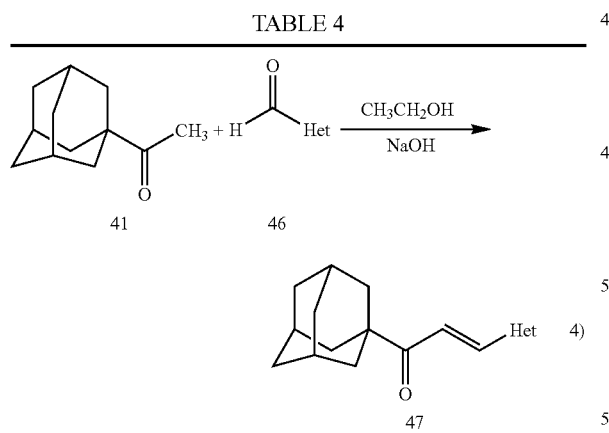

Chalcone-Like Compounds 47 Synthesized with Aromatic C Ring Subsituted by Heterocyclic Ring

| Compd | HET | % YIELD | MP ° C. |
|---|---|---|---|
| 47a | Pyrid-2-yl | 72 | 94.4-97.5 |
| 47b | Pyrid-3-yl | 81 | 105.7-106.9 |
| 47c | Pyrid-4-yl | 85 | 125.7-127.5 |
| 47d | 6-methylpyrid-2-yl | 54 | 119.1-120.3 |
| 47e | Quinol-4-yl | 64 | 120.8-122.0 |
| 47f | Quinol-3-yl | 71 | 157.0-159.0 |

TABLE 4-continued

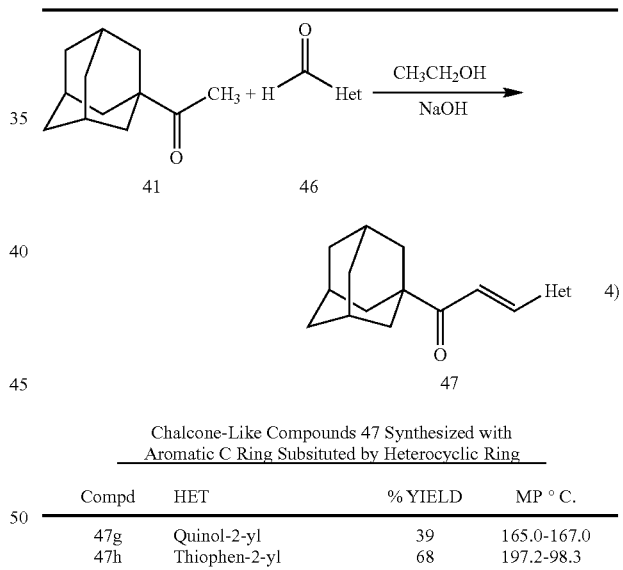

Chalcone-Like Compounds 47 Synthesized with Aromatic C Ring Subsituted by Heterocyclic Ring

| Compd | HET | % YIELD | MP ° C. |
|---|---|---|---|
| 47g | Quinol-2-yl | 39 | 165.0-167.0 |
| 47h | Thiophen-2-yl | 68 | 197.2-98.3 |

Series IV. Synthesis of Chalcones 58 with Adamantane Moiety Substituted on Ring A This series of compounds was prepared to study the effect of the adamantane moiety as a substituent on the aromatic A ring. In order to do this we had to prepare the appropriate aryl adamantanes prior to carrying out the Aldol condensation.

Synthesis of Aryl Adamantanes 50 Adamantylation of aromatics has not been frequently studied, in spite of its potential importance. Testafari and coworkers studied adamantylation of aromatics in a radical reaction with the 1-adamantyl radical to describe the effect of substituents on the reactivity and isomer distribution. Newman first reported the AlCl₃-catalyzed Friedel-Crafts alkylation of benzene with 1-bromoadamantane, where a complex product mixture was obtained (eq 5).

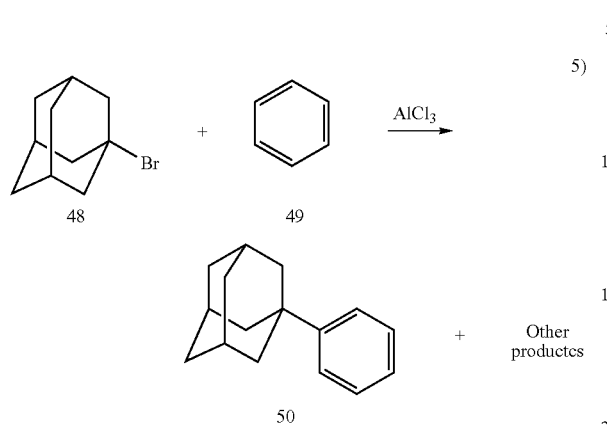

Later the adamantylation of reactive aromatics with adamantyl nitrate and a $FeCl_3$-catalyzed reaction was described using an excess of the aromatic compound. In the case of toluene as substrate exclusive formation of para-adamantylated product was reported. The study of Friedel-Crafts adamantylation of benzene and toluene in the presence of boron tris(triflate) has also been reported (eq 6).

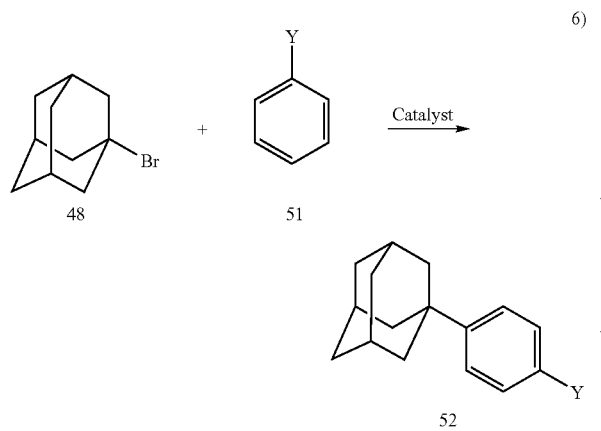

All attempts at adamantylating nitrobenzene were unsuccessful, as expected. The nitro substituent is a strong electron withdrawing group thus greatly decreasing the reactivity of the aromatic system towards electrophiles.

Iron filing-catalyzed Friedel-Crafts alkylation of aromatic compounds with 1-bromoadamantane 48 is unknown. However, the use of iron as a Friedel-Crafts catalyst in alkylation of aromatic systems has been described in the literature. In this study, a novel methodology for the adamantylation of benzene 49 and some of its derivatives has been discovered. One of the most remarkable features of this reaction is the ease of product separation from the iron catalyst by simple filtration. Moreover, no usual aqueous basic work-up is necessary.

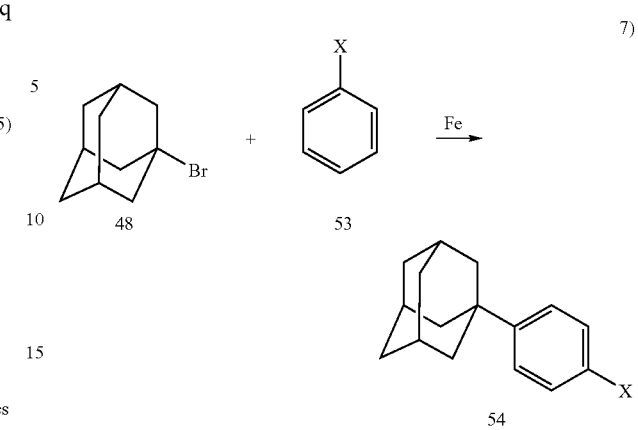

This particular adamantylation reaction appears to be versatile as to what type of catalyst can be used. Iron (0), Iron (II) oxide and iron (III) oxide does give the Friedel-Crafts products in very good yields.

TABLE 5

Some 1-Aryladamantanes 54 Synthesized By this Method

| Compd | X | % YIELD | Mp ° C. |
|-------|-----|---------|-----------|
| 54a | H | 90 | 87.3-88.9 |
| 54b | Me | 93 | 95.3-98.9 |
| 54c | OMe | 95 | 78.4-81.3 |

Given that these Friedel-Crafts type alkylation reactions are expected to proceed via cationic intermediates, then it is reasonable to expect Fe to be an effective catalyst. 1-aryladamantanes 54 were prepared by heating (boiling temperature of the reacting aromatic system) the reaction of 1-bromoadamantane 48 with substituted benzenes 53 in the presence of Fe (eq 7). The experimental results show that the reaction rates decrease significantly in parallel with the decrease in reaction temperature. The adamantylation reaction does not take place at room temperature.

As evidenced by the experimental data presented in Table 5 this synthesis indeed produced very pure product in excellent yields. The mechanism for this reaction appears to be ionic as confirmed by the stereochemistry of the Friedel-Crafts alkylation products. For instance, electron withdrawing substituents on the aromatic system yield exclusively the meta-substituted derivatives, whereas electron donating susbtituents afford the corresponding para-substituted products. It is worth noticing that only the para substituted isomer is observed. The significant differences in the stability of ortho and para isomers can be explained by the strong steric interaction between the ortho substituent and the bulky adamantyl group. Thus preventing the formation of the ortho isomer. These products were fully characterized by GC-MS, proton and carbon-NMR. The results described herein also agree with monoadamatylated products synthesized by Olah et al. In addition, Engel et al found the formation of bi-adamantane in yields of at least 20% when forcing the mechanism to follow the free radical pathway in the presence of AIBN and tributyltin. These reagents are well known to induce the formation of free radicals. In this work, no bi-adamantane was detected thus indicating that mechanism for the Fe catalyzed Friedel-Crafts adamantylation proceeds via ionic pathway.

It is well known that 1-adamantyl cation is a stable bridgehead carbocation. This carbocation is formed by reacting bromoadamantane with a Lewis acid catalyst and attacking by the aromatic system in a traditional Friedel-Crafts way. The substitution pattern will determine whether the mechanism is via a free radical or ionic. A series of simple experiments were designed in order to study the stereochemistry of the products thus determining the preferred mechanistic pathway.

Electron donating substituents favor meta substitution on the aromatic ring when the reaction is proceeding by a free radical mechanism. In addition, electron withdrawing groups favor ortho/para substitution when following similar pathway. However, electron donating substituents favor ortho/para substitution and electron withdrawing substituents favor meta substitution when the reaction takes place via an ionic mechanism.

Solid acid catalyzed Friedel-Craft adamantylation reactions have been found to be a convenient methodology for the preparation of adamantyl-substituted aromatics with high para-regioselectivity. DeMeijere et al. has utilized palladium/charcoal mixed with potassium carbonate as catalyst for Friedel-Crafts adamatylation reactions. His team of researchers has proved the mechanism for such reaction is ionic. However, the times for the reactions to take place tend to be mildly lengthy (from 12 to 24 h) and in some instances, regardless of the electronic nature of the substituent on the aromatic system, some of the desired products are not formed.

The methodology described in this work makes use of much milder conditions affording high yields of adamantylated products. The iron catalyzed Friedel-Crafts adamantylation presented herein does have a great advantage over the literature procedure due to the facility of handling the reactants, the relatively low prices of the starting materials, and the easyness in extracting the final products with high degree of purity (in some instances, crystals form after filtration and washings with hexane). An example is compound 54c.

The fragmentation pattern for 1-arylsubstituted adamantanes follows a different process than that of 1-alkylsubstituted adamantanes. Usually, and in these cases all three compounds follow the same behavior, adamantane fragments itself into an aromatic (benzene) unit losing a $C_4H_9$ fragment (m/e 57), thus leaving behind a benzene-aromatic fragment as a base peak.

Synthesis of 5-(1-adamantyl)-2-methoxy Acetophenone 55. This acetophenone 55 was synthesized from the anisole 54c by Friedel-Crafts acylation prior to preparation of the chalcone derivatives by Aldol condensation. Friedel Crafts acylation is known to perform well if the substituent is an electron donating group. Compound 54c was selected since it best exhibited this quality.

The 1-aryladamantane 54c was converted to 5-(1-adamantyl)-2-methoxy-acetophenone 56 by treatment with acetyl chloride in the presence of $AlCl_3$ as a catalyst at room temperature (eq. 9)

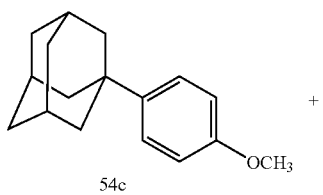

54c

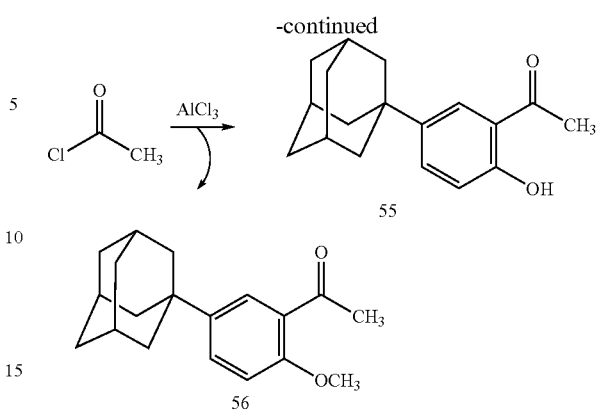

Synthesis of the Chalcone 58. After considering that the resonance effect in aromatic compounds increase biological activity, chalcone 58 was synthesized. Treatment of the resulting product 55 with biphenyl benzaldehyde 57 as described previously to give 58 (eq 10).

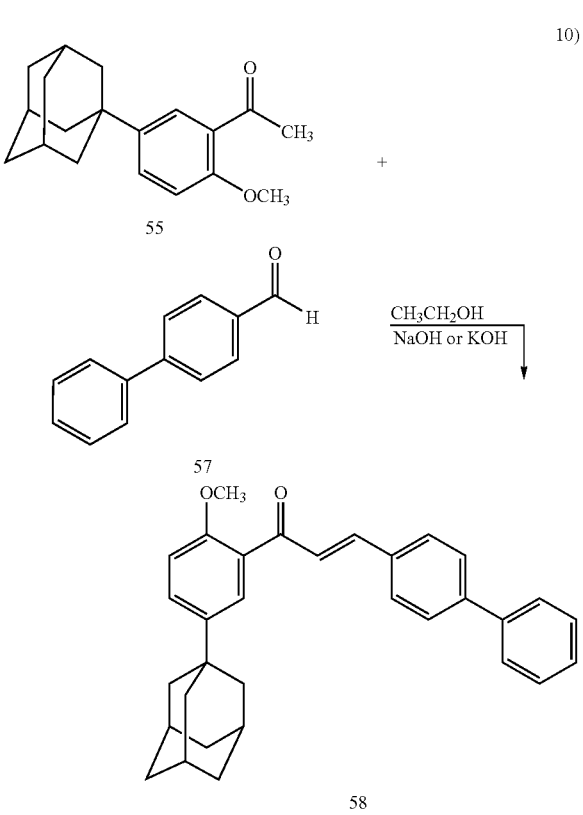

In this study we have synthesized a wide variety of compounds and have identified several chalcone-like compounds, which possess growth-inhibitory activity against selected cell lines, particularly breast cancer cell lines. Some of the chalcone-like compounds (series III), which have quite different chemical structures from conventional chalcones, show higher activity against breast cancer cell lines than chalcones. Screening of these compounds on breast cancer cell lines has been conducted in vitro, and the data are presented in the sections that follow.

Two types of antiestrogens are the analogs of tamoxifen or structural derivatives of the triphenylethylene type of drug. All of these compounds are inhibitors of the binding of E2 to the ER, but there the similarity ends. Antiestrogens seem to form a receptor complex that is converted incompletely to the fully activated form. As a result of the imperfect changes in the tertiary structure of the protein, the complex is only partially active in initiating the programmed series of events necessary to orchestrate gene activation.

Studies in vitro demonstrate that very low concentrations of triphenylethylene-type antiestrogens can cause a single round of replication in breast cancer cells, but high concentrations of these antiestrogens are completely inhibitory. It is possible that the modest partial estrogen-like action at low concentrations causes the tamoxifen flare that sometimes is observed when therapy is started in patients with bony metastases. Once steady-state levels of the drug have been achieved (approximately 4 to 8 weeks with 20 mg/day), symptoms will have disappeared and the patient will experience a response to therapy. It is important therefore, to be able to identify tumor flare and not prematurely terminate a beneficial therapy. Nevertheless, a recent report has demonstrated that clinicians often prematurely terminate antiestrogen treatment based on changes in bone scintigraphy misinterpreted as progressive disease. Because there are toxicological advantages in disease control with antiestrogens, a premature change to chemotherapy may be inappropriate.

The interactions of the ER with EREs also depend on the nature of the ligand to which it has bound. When the effects of binding of estrogenic and different antiestrogenic ligands to an ERE are quantitated, it was found that E2-ER and 4-OHT-ER complexes bound a singlet ERE with similar affinity. However, at saturation, 4-OHT-ER binds 50% the level of E2-ER binding. When the tandem copies of EREs were tested, E2-ER exhibited cooperative binding whereas 4-OHT-ER displayed little or no cooperativity. Therefore, specific ligand binding can alter binding affinity of the ER to DNA and the amount of receptor that is saturated presumably by inducing different conformations in the ER protein. Further studies of the mechanism through which antiestrogens antagonize the transcription of estrogen-responsive genes through differential binding to EREs show that the flanking sequences and stereoalignment of EREs are important.

A further investigation of antiestrogenic ligands demonstrated that when 4-OHT-ER binds to DNA one molecule of 4-OHT dissociates from the ER dimer. Under the same conditions, tamoxifen aziridine, which covalently attached to the ER, show a binding stoichiometry identical with that of E2-ER, which is one dimeric receptor per ERE compared with one monomer of 4-OHT-ER per ERE. When DNA footprinting was used to determine ER-ligand binding to adjacent EREs, identical high-affinity binding was observed for unliganded dimeric ER or ER bound to E2,4-OHT, and tamoxifen aziridine. These results suggest that ligand-induced conformation changes primarily affect how the ER interacts with the components of the transcription initiation complex thereby mediating transcriptional activation.

The compounds of the present invention were evaluated by comparing breast cancer cell lines MCF-7 (ER-positive) and MDA-MB435 (ER-negative) with noncancerous breast epithelial cells (MCF-10). Those compounds that showed a high level of antiproliferative activity against tested breast cancer cell lines, but not against normal breast epithelial cells were evaluated for in vitro mechanism of action by looking at their effects against cellular growth factors, Epidermal Growth Factor (EGF), and Transforming Growth Factor (TGF-alpha).

Biological activities (anti cancer) were measured under the following conditions:

1. A dose response curve for compounds, series I, II, III, IV, over a concentration range of 1 mM to 1 nM was prepared in order to detect the doses where possible biological activity might exist. Biological activity was determined by relative $LC_{50}$ values of these agents. Those compounds that exhibited significant decreased cell viability within the established concentration range parameters were examined for their relative biological activity and potency against known antibreast cancer agents tamoxifen, genistein, and doxyrubicin.

2. The compounds in series I, II, III, and IV were examined against two different types of breast cancer cell lines which included estrogen receptor positive (MCF-7) and estrogen receptor negative (MDA-MB435) cell lines. This examination allowed our laboratory to determine whether the novel agents exhibit relative selectivity for estrogen stimulated breast cancer cell lines versus estrogen non stimulated breast cancer cell lines.

3. Toxicity of the compounds for normal breast epithelial cells were examined by comparing $LC_{50}$ values in normal breast epithelial cell line (MCF-10) against $LC_{50}$ values in cancer cell lines. $LC_{50}$ is the concentration that is lethal to 50 percent of the cells. $LC_{50}$ values were estimated from a dose response graph.

4. The possible mechanism of action of these compounds was explored by examining the ability of these agents to reverse growth factor stimulated proliferation. The ability of these compounds to attenuate EGF and TGF stimulated growth was tested.

By examining these parameters, our laboratory was able to determine whether these novel agents possess any antiproliferative activity against specific breast cancer cell lines MCF-7 (ER-positive) and MDA-MB435 (ER-negative) or toxicity towards noncancerous breast epithelial (MCF-10). Further, by pursuing this examination our laboratory was able to determine to some extent that certain structural modifications enhance the biological activity and/or potency of these compounds.

Two human breast cancers cell lines (MCF-7 and MDA-MB435) and a normal breast epithelial cell line (MCF-10) were obtained from ATCC (American Type Culture Collection) to test against the series of compounds and the data were examined for the compounds' relative antiproliferation profiles. All of these cell lines were derived from epithelial tissue. These cell lines were selected because they allowed our laboratory to investigate the effects of the compounds in: 1) breast neoplasms whose growth is stimulated by the presence of estrogen, MCF-7 (ER-positive); 2) Breast neoplasms whose growth is not stimulated by estrogen MDA-MB435 (ER-negative); and 3) A non-cancer cell line (MCF-10) to compare relative toxicities of the compounds.

It has always been difficult to obtain cultures of breast tumor cells from primary mammary tumors because the presence of fibroblasts, and fatty and lymphocytic tissue make it difficult to isolate the mostly epithelia breast tumor cells. Even when such cells are isolated, there is only a low number of viable tumor cells in solid tumors. Cell lines have been successfully established from pleural effusions, however. Pleural effusions arise from metastasizing tumors and are found in the cavity between lung and the chest. The fact that the tumors are metastasizing probably indicates the presence of more active cells, and the cells in the pleural effusion may somehow have adapted to a liquid environment.

Most of the human breast cancer cells in continuous culture are of epithelial origin. MCF-7 cells were obtained by growing a primary culture from a pleural effusion of a patient with an infiltrating ductal carcinoma. This primary culture continuously produced free-floating cells that were used to initiate the stable MCF-7 cell line. This cell line possesses high affinity for estradiol, which stimulates its growth. It also has the insulin receptor but there are conflicting reports about growth induction by insulin.

General Screening Results

The following sections present the findings of the biological screening assays for the series I, II, III, and IV compounds. These experiments dealt with non-stimulated cell growth and the ability of the synthetic compounds to alter the viability of these cells.

EXAMPLE 1

Series I compounds were chalcone like-compounds where the A ring has been replaced by the adamantyl moiety. Various concentrations of these compounds were added to cancer cell lines and biological activity was measured as detailed in the experimental section.

Series I compounds demonstrated limited activity on the viability of MCF-7 cell, with the exception of 43f which exhibited a pronounced effect on cell viability at concentrations greater than $10^{-5}$ M. At these concentrations, 43f decreased cell viability 20 percent. These series of compounds produced similar effects on MD-MBA435 cells. However, 43f altered cell viability only at much higher concentrations than required for MCF-7 cells.

EXAMPLE 2

Series II compounds are chalcone like-compounds with a modification on the A ring and the B region, where the A ring has been replaced by the adamantyl moiety and the addition of a double bond to the B region. Various concentrations of these compounds were added to cancer cell lines and biological activity was measured as detailed in the experimental section.

Series II compounds demonstrated little activity in altering the viability of MCF-7 cells. 45a produced a small attenuation in the viability of these cells, while other members of these series were in effective.

EXAMPLE 3

Series III compounds are chalcone like-compounds where the A ring has been replaced by the adamantyl moiety, and the C ring replaced by a heterocyclic group. A dose response analysis was performed for these compounds to determine their cytotoxic properties as specified in the experimental section.

Compounds, (47a-e), were found to show significant anti-cancer activity against the MCF-7 cell lines. The $LC_{50}$ values for series III (50 µM, 40 µM, 50 µM, 5 µM, and 0.5 µM respectively) were consistently lower than the $LC_{50}$ values of known anti-breast cancer agents: Tamoxifen, Doxyrubicin, and Genestein, indicating higher potency. As demonstrated herein, the compounds in series III were consistently more effective at lower concentrations (<10 µM) than the known anti-cancer agents with compounds 47-c and 47-e showing the greatest efficacy. Three compounds (47a-c) in series III demonstrated significant anti-cancer activity against MDA-MB435 cells, with $LC_{50}$ values of 1 µM, 5 µM, and 50 µM respectively. Known anti-cancer agents tamoxifen and Genestein were measurably less potent in MDA-MB435, with $LC_{50}$ values of 0.5 mM and 5 mM respectively. (No measurable $LC_{50}$ was obtained for Doxorubicin in the concentration range measured).

These three compounds demonstrated greater activity compared to Doxyrubicin and Genestein at concentrations between 10 nM and 0.1 µM, and greater potency at higher concentrations. Tamoxifen demonstrated similar activity to our synthesized compounds only at concentrations above 0.1 mm, but was ineffective at lower concentrations. Compounds 47-d and 47-e proved to be less promising against MDA-MB435 cells. For compound 47-e, an $LC_{50}$ value of ca 5-mM was obtained, for compound 47-d, no $LC_{50}$ value was obtained in the concentration range measured. Tamoxifen and Doxyrubicin were measurably less potent against these cells ($LC_{50}$ values of 0.5 mM and 5 mM, respectively). In the concentration range tested, no $LC_{50}$ was obtained for Genestein.

The relative toxicity of the synthesized compounds (47a-e) against normal breast cells was studied by exposing normal breast epithelial cell line MCF-10 to our synthesized compounds in concentration ranges from 1 nM to 1 mM. These cells were likewise exposed to equivalent concentrations of Tamoxifen, Genestein, and Doxyrubicin. Series III synthesized compounds did not significantly decrease the average percent cell viability, which was maintained near one hundred percent, at lower concentration of these compounds. At concentrations lower than $10^{-7}$ M, these compounds appeared to enhance the viability of cells.

EXAMPLE 4

Series IV synthesis was directed to chalcone compounds where the A ring has an adamantyl moiety. A dose response analysis was performed for a compound within this series to determine its cytotoxic properties, as specified in the experimental section. This compound showed no biological activity at low concentrations, but exhibited a small decrease in cell viability at concentration greater than $10^{-5}$ with MCF-7 cells.

Chalcones and isoflavone compounds, such as Genestein, have been cited to exhibit anti-breast cancer activity, mostly against ER positive breast neoplasms. Antiestrogens, such as tamoxifen, are effective in controlling the growth of estrogen receptor positive breast tumors. Doxyrubicin, an alkylating agent is a general anti cancer drug that can be administered for the treatment of breast cancer.

All of these antineoplastic agents were selected as standards to compare with the novel chalcone-substituted adamantane compounds (47a-e) for their relative anticancer activity against human breast cancer cell lines MCF-7 (ER-positive) and MDA-MB435 (ER-negative). The compounds were also examined for their relative toxicity against normal breast epithelial cell line MCF-10. In order to detect the concentrations at which the (47a-e) compounds exhibited an anti breast cancer activity, a concentration response curve was generated from 1 mM to 1 nM. This concentration range was able to give us a broad spectrum of ability to decrease the percent of cell viability of the two human breast cancer cell lines.

In the initial evaluation novel adamantane substituted chalcone derivatives, five of these compounds exhibited significant anti-breast cancer activity against MCF-7 cells, over the tested concentration ranges. Compounds (47a-e) decreased the % cell viability of MCF-7 by 50% with $LC_{50}$ values of 5 mM, 1 mM, 0.5 mM, 0.5 mM, and 50 µM, respectively. 47-e (50 µM) proved to be the most potent analog against MCF-7 cells compared to the other active analogs. This suggests an important moiety modification in the chalcone skeleton structure that can enhance the potency of the chalcones-like derivatives. Genestein is an isoflavone that is a precursor to chalcone molecules. Therefore the comparison of (47a-e) compounds to Genestein for anti breast cancer activity was paramount.

The results indicated that the novel (47a-e) compounds were more effective than Genestein in increasing the percent cell death of MCF-7 cells. This suggests that the adamantane substitutions were an important modification to the chalcone skeleton in terms of enhancing biological activity. $LC_{50}$ concentrations demonstrated that 47-e was more potent than tamoxifen, inducing 50% cell death in MCF-7 cells at concentrations of 50 µM and 0.5 mM, respectively. Two compounds, 47-c and 47-d, had comparable $LC_{50}$ values with tamoxifen. At high concentrations (1 mM) all eight compounds, except 47-b and genestein, induced cell death in excess of 70% in MCF-7 cells, indicating potential cytotoxic effects.

Although the $LC_{50}$ value of 47-e only represented a 10-fold increase in % cell death over that obtained for tamoxifen, it nevertheless demonstrated a consistent concentration response curve in contrast to tamoxifen's sudden change in slope. At concentrations lower than 1 nM, 47-e was significantly more potent than tamoxifen. Compounds 47-d and 47-c likewise showed a graded response curve, and exceeded tamoxifen potency below 0.1 mM.

Compound 47e was also found to be more potent than doxorubicien against MCF-7 cells at $LC_{50}$ concentrations of 10 µM and 0.5 mM, respectively. 47-c and 47-d were equally potent as doxorubicien. Doxorubicien has been reported to exhibit general anti breast cancer activity, with no specificity for ER-positive vs. ER-negative breast cancer neoplasms. Therefore, doxorubicin serves as a neutral anti neoplastic agent in the in vitro anti breast cancer screening procedure.

Compounds 47 a-c, e also exhibit anticancer activity against human breast cancer cell line MDA-MB435, with $LC_{50}$ values of 5 µM, 5 µM, 5 µM, and 1 mM, respectively. The anti breast cancer activity exibited by 47 a-c against MDA-MB435 cells represented a 1000 fold increase in potency over both Genestein and Tamoxifen (each with $LC_{50}$ values of 5 mM). The third known anticancer agent, Doxorubicin demonstrated no detectable $LC_{50}$ value in the concentration range measured.

These results are not suprising, considering that Genestein is found to be selective for estrogen receptor positive breast cancers, and that tamoxifen has been found to induce sensitivities toward a subpopulation of ER-positive breast tumors. However, based on the enhanced potency of these chalcone-like compounds (series III compounds) vs. structurally similar Genestein, the substitutions of adamantane moieties indicate an important substitution in designing potential anti breast cancer agents with chalcone like skeleton structures.

By $LC_{50}$ values, 47e demonstrated a significant decrease in percent cell viability against MDA-MB435 cells compared to its efficacy towards MCF-7 cells. Also, 47d caused a significant decrease in percent cell viability in MDA-MB435 cells as compared to MCF-7 cells, with undetectable $LC_{50}$ values in the tested concentration ranges. These significant changes in specificity for ER-positive and ER-negative human breast tumors could represent important structural modifications with chalcone skeletal structures that changes allows this group of chalcones to be directed towards ER-negative vs. ER-positive breast neoplasms.

Compounds 47 a-e were all tested for their relative toxicities against a normal breast epithelial cell line MCF-10. At the highest concentrations tested (1 mM), none of the series III compounds decreased the % cell viability of MCF-10 cells below 80% with average values of 103, 124, 102, 94, and 98, respectively. This effect demonstrates the selective ability of these novel compounds to significantly affect the growth of cancer cells without interrupting the mechanisms involved with proliferation of normal breast epithelial cells.

In summary, the results indicated that the novel chalcone-like compounds (47a-e) significantly increased ($p<0.01$) the cell death of both human breast cancer cell lines MCF-7 (ER-positive), and MDA-MB435 (ER-negative), without altering the viability of normal breast epithelial cell line MCF-10.

Antiestrogens and Growth Factors

During the past 20 years, considerable focus has been put on the mechanisms whereby cells modulate the growth stimulus or stop growing when the task of replication is complete. The identification of families of stimulatory or inhibitory growth factors that affect the same cell (autocrine factors) or adjacent cells (paracrine factors) has revolutionized the concepts of hormonal regulation. The ideas have been translated during the past decade from general physiology to be applied to cancer control.

Transforming Growth Factor α

Estrogen is believed to increase the production of TGFα and, through autocrine activation of the epidermal growth factor receptor, encourage replication. However, TGFα alone cannot substitute for estrogen. MCF-7 cell transfected with the cDNA for TGFα are not tumorigenic in athymic mice.

Studies by Wakeling and colleagues compared the ability the antiestrogen tamoxifen or its active metabolite, 4-OHT, to attenuate the stimulatory effects of TGFα on MCF-7 cells. They showed that when MCF-7 cells are treated with TGFα, tomaxifen partially blocks the stimulatory effect in the absence of E2. In contrast, studies using EGF instead of TGFα showed that antiestrogens could not block the actions of the growth factor, and also that antiestrogens could not block the paracrine influence of ER-negative cells from stimulating MCF-7 cells in vitro. In addition, it is known that estrogens can induce the expression of TGFα in estrogen-responsive breast cancer cell lines, whereas antiestrogens generally decrease TGFα expression in vitro and in vivo.

TGFα apparently is essential for estrogen-stimulated, anchorage-independent growth. TGFα or epidermal growth factor receptor antibodies can negate the E2-stimulated, anchorage-independent growth of MCF-7 cells on soft agar. The antibodies did not affect progesterone or prolactin.

The effects of antiestrogens on TGFα expression in vivo have not been studied extensively; however, one study shows that tamoxifen is capable of down-regulating tumor TGFα expression in postmenopausal women with ER- and PR-positive disease but not in women with ER- and PR-negative disease.

The regulation of TGFα remains unclear. A few putative half-site EREs have been identified in the promotor region of the TGFα gene, but other sites in the promotor region are required for gene activation. Constructs of the EREs alone do not appear to respond to estrogen action unless the cells are super-transfected with ER. By contrast, ER-negative cells that are stably transfected with ER will induce TGFα mRNA in response to estrogen.

Perhaps, most interesting is the effect of antiestrogens. Raloxifene acquires the ability to initiate TGFα synthesis when ER-negative cells are stably transfected with a 351-mutant ER. However, in ER-negative transfectants containing wild-type ER, raloxifene is a complete antiestrogen. 4-OHT acts as an estrogen (induction of TGFα) in both wild-type and mutant ER stable transfectants. Because antiestrogens produce different effects in transfectants expressing wild-type or mutant ER, and because 4-OHT and estrogen can both initiate TGFαmRNA transcription equally, this provides a unique model to determine which proteins associate with the antiestrogen-ERE complex to make it so promiscuous.

Transforming Growth Factor β

The TGFβ family of inhibitory polypeptides consists of three or more 25 kDa members, which are able to homo- or heterodimerize to form complexes that interact with the TGFβ receptor (TGFβR). These peptides are implicated in breast cancer and have been found to be over-expressed and correlate with tumor progression. TGFβ binds to any of the different characterized TGFβRs. The receptor consists of a heterodimeric complex, one part of which is a binding protein that is unable to signal and another part that is believed to transduce signals to the cell through serine-threonin kinase activity. The ability of TGFβ to promote tumor progression is counterintuitive because TGFβ usually produces either growth inhibition or differentiation, neither of which are involved in tumor progression. Further study clearly is needed in vivo to determine what cooperating factors dictate the effects of TGFβ on different cell types, because the results may be critical to understanding the success or failure of antiestrogen therapy.

The effect of tamoxifen on the production of TGFβ is an area of great interest. Elucidation of a mechanism could provide an explanation for the cell cycle effects of tamoxifen in ER-positive cells and also provide an explanation for the sporadic reports of the success of tamoxifen treatment in ER-negative breast cancer. Much work has been completed in cell culture but there are important translational aspects of the research that are relevant in understanding the action of tamoxifen.

Tamoxifen has a direct effect on the production of TGFβ in breast cancer cells. TGFβ expression increases in MCF-7 cells, and further study has shown a differential activation of members of the TGFβ family. However, the results are variable. Some studies report an increase in TGFβ-2 with tamoxifen, whereas others demonstrate rises in TGFβ-1. This observation has been translated to the clinic. Patients that respond to tamoxifen therapy show increases in TGFβ-2 plasma levels. Knabbe's study suggests that the results of measuring either TGFβ-1 levels (which transcriptionally activates TGFβ-2) or TGFβ-2 in the plasma can be used as a predictive test for the efficacy of tamoxifen therapy.

Some support for the central role of TGFβ-2 comes from sampling tumors directly. When TGFβ mRNA levels from ER-positive breast tumors were monitored before and during tamoxifen therapy, the results were variable. Changes in TGFβ-1 and TGFβ-2 did not correlate with tamoxifen treatment, but there was a significant correlation between treatment and changes in TGFβ-2 in some tumors. The authors concluded that response to tamoxifen therapy might be mediated through an increase in the expression of a particular TGFβ iso-form.

The effect of tamoxifen on ER-negative tumors is far more controversial. Perry and coworkers have compared and contrasted the effect of tamoxifen on the induction of TGFβ-1 in an ER-positive and an ER-negative cell line. After long-term treatment, the expression of TGFβ-1 increased, independent of ER status, but an accumulation of cells in G1/G0 and an increase in apoptosis occurred concurrently. This conclusion tends to support a model of the direct effect of tamoxifen on ER-negative cells.

By contrast, it is possible that the growth of an ER-negative cell is controlled by a paracrine mechanism. Perhaps the ER-positive cell produces TGFβ in response to tamoxifen, but the secreted growth factor stops the growth of the adjacent ER-negative cells. It is known that ER-negative breast cancer cells have a high density of TGFβ receptors, and the cells respond to TGFβ by growth inhibition. The hypothesis that an ER-positive cell can control the growth of ER-negative cells during tamoxifen therapy has been demonstrated in vitro. However, this has not been possible to test in animal models. Different mixes of ER-positive and ER-negative cells were inoculated into athymic animals and treated with the antiestrogen toremifene. Regrettably, in model, the antiestrogen was unable to control heterogeneous tumor growth.

However, the laboratory finding that tamoxifen can induce TGFβ in fibroblasts has introduced a new mechanistic dimension to understand the control of ER-negative disease by tamoxifen. Clearly, if TGFβ can be induced in the supporting stromal cells of a breast cancer tumor during tamoxifen therapy, the paracrine growth inhibitor could control the proliferation of ER-negative cells. Butta and coworkers found that TGFβ production increases in stromal cells during tamoxifen therapy. Although these data illustrate that a complex cellular conversation occurs to regulate cell growth, the fact that tamoxifen is not usually successful in ER-negative disease means that the pathways are not necessarily dominant. Nevertheless, the realization that TGFβ can act both as a growth inhibitor and as a growth stimulator may ultimately make the pathways important to explain tamoxifen failure.

In summary, the past decade has seen an elucidation of the role of both positive and negative growth factors in estrogen-stimulated growth. Although each effect of tamoxifen on the growth factor system may in itself be small, it is possible that the combined actions of tamoxifen are responsible for the benefits documented with tamoxifen in clinical practice.

Screening Using the Growth Factor Protocol

The mechanism of the specificity for breast cancer cells vs. normal breast epithelial cells has not been established. In order to elucidate the mechanisms, by which these novel series III compounds were able to exert their effects against both MCF-7 and MDA-MB435 cells, the two cells were examined for common receptors that might be involved in cell proliferation. It is known that both cell lines expressed epidermal growth factor receptors (EGFR). Also both cell lines are sensitive to epidermal growth factor (EGF) ligands and Transforming Growth Factor alpha (TGF-α).

There have been several studies that have examined the relative changes in expression of EGF, EGFR, and TGF-α in estrogen receptor positive vs. estrogen receptor negative breast cancer cell lines. These changes in growth factor expression were correlated with the stimulation or inhibition of cellular proliferation. Also there have been several studies that demonstrate that the isoflavone class of compounds exert their anti breast cancer effects by altering the EGF, and EGFR proteins. Because of the structural similarity of these isoflavones and chalcones to naturally occurring estrogens, it was initially suggested that these isoflavones might prevent hormone-dependent breast and prostate cancers by virtue of their potential estrogen-antagonist activity. Human breast cancer (MCF-7) cells, when placed ectopically in ovariectomized adult rats, grew at a faster rate in rats fed genestien-containing diets than in those fed control diets, yet another indication of the estrogenic activity of genistein.

In cell culture, genistein inhibited proliferation of human breast and prostate cancer cells stimulated by epidermal growth factor (EGF) independently of whether the cells expressed estrogen receptors. In the presence of 17β-estradiol, genistein induced no additional proliferation at any concentration examined. Instead, at concentration >5 μmol/L it caused a dose-dependent reduction in the 17β-estradiol-stimulated cell proliferation. These data indicated that genistein may inhibit cell proliferation by mechanisms other than classical estrogen-receptor-mediated pathway. Genistein cannot, therefore, be viewed simply as either an agonist or antagonist of estrogen. Understanding the biological effects of genistein in vivo also requires an appreciation of all of its mechanisms of action. Therefore, the novel series III compounds were evaluated for their relative abilities to reverse the growth stimulatory effects of EGF and TGF.

Concentration of genistein that inhibit proliferation of human breast cell lines do not effect phosphorylation of EGFR or other target proteins which are normally stimulated by EGF. Normal human mammary epithelial (HME) cells (which do not express estrogen receptor) stimulated by EGF are exquisitely sensitive to growth inhibition by genistein without any inhibition of EGF-R tyrosine autophosphorylation; the concentration at which cell growth is inhibited by 50% (IC50) is 1 μmol/L. These data strongly suggest that genistein affects these cells (and therefore other systems) by mechanisms other than inhibition of PTK activity.

In a glioblastoma model in vitro, both invasiveness and proliferation of glioblastoma cells were dependent on EGF, but the invasiveness was blocked by genistein at concentrations that did not affect proliferation or EGF-R autophosphorylation. These data provide compelling evidence of 2 subsets of activities modulated by EGF-R, only one of which is affected by genistein.

Both MCF-7 and MDA-MB435 cells contain EGF-R and TGF-R. In an effort to examine the role of EGF-R and TGF-R in the proliferation of MCF-7 and MDA-MB435, these cells were stimulated to growth stimulatory at 50 percent ($GS_{50}$) values. The cells were treated with the synthesized compound 47a at concentrations ranges of $10^{-9}$ to $10^{-3}$ M.

EGF-Serum and Non-Serum Stimulated Growth of MCF-7 Cells

The results indicated that EGF-serum stimulated growth of MCF-7 cells was significantly (p<0.02) reversed back to control values by 47a at 10 μM. EGF-non serum stimulated growth was also significantly (p<0.102) reversed back to control values by 47a at $IC_{50}$ values of 50 μM.

TGF-α Serum and Non-Serum Stimulated Growth of MCF-7 Cells

The next experiment was performed to examine the possible role of TGF-α in the proliferation of MCF-7 cells. The results indicated that neither TGF-α serum stimulated nor non-serum stimulated growth of MCF-7 cells significantly reversed by 47a at concentration ranges of $10^{-9}$ to $10^{-3}$ M.

In evaluating the ability of 47a to inhibit the EGF growth stimulation of MCF-7 cells, compound 47a significantly reversed the growth stimulatory effects of EGF, but not TGF-α.

This could possibly indicate a selective mechanism by which this drug exerts its inhibitory effects against MCF-7 cells. The results indicate that the EGF serum and non-serum stimulated growth of MCF-7 cells were inhibited by 47a in a similar manner. This could indicate that the inhibition seen by EGF-serum stimulated growth was mainly due to inhibition of EGF-stimulation. The fact that there was little or no reversal on TGF-α serum or non-serum growth stimulation indicates the selectivity of 47a for EGF in serum stimulated growth.

TGF-α and EGF Serum and Non-Serum Growth Stimulation of MDA-MB 435 Cells.

Compound 47a was evaluated for its relative ability to reverse the $GS_{50}$ stimulation of MDA-MB 435 cells by TGF (1 ng/ml). The results indicated that the TGF significantly (p<0.02) reversed the serum and non-serum stimulated growth of MDA-MB 435 cells back to control values at 50 μM and 10 μM, respectively.

Neither EGF (1 ng/ml) serum nor non-serum stimulated growth of MDA-MB435 cells was reversed by to control values at concentration ranges of $10^{-9}$ to $10^{-3}$ M. This data seems to indicate the relative importance of the TGF-R in MDA-MB435 cells.

Comparing the TGF-α serum to non-serum profiles seems to imply that 47a is able to decrease the cell viability of MDA-MB435 cells by interfering with the TGF-α mediated growth stimulation of MDA-MB435 cells.

The data seems to suggest that one of the possible mechanisms by which 47a might decrease the cell viabilities of the two human breast cancer cell lines is to reverse the epithelial growth stimulatory effects induced by growth factors EGF and TGF-α. Literature suggest that these factors play a key role in the proliferation of epithelial cells. At concentration ranges of 1.00 to 50 μM, the compound 47a reversal effects back to control values correlate with $LC_{50}$ values obtained by drug treatment. Although this reversal may not indicate the total mechanism by which the series III synthesized compounds exert their effects on the human breast cancer cell lines, but they approximate a quantitative possibility for their relative mechanism of action.

The results of testing the compounds of the present invention indicate that alterations in EGF-R stimulation is a key mechanism by which series III compounds decrease the cell viability of MCF-7 cells. This is in agreement with current literature, which indicates an important connection between estrogen and epidermal growth factors.

In an effort to elucidate possible mechanisms of action that our synthesized compounds exhibited against MCF-7 and MDA-MB435 breast cancer cell lines, 47a (the parent compound) was evaluated for its relative ability to reverse the growth stimulation at 50% of MCF-7 and MDA-MB435 cells by serum and non-serum stimulated epidermal growth factor (EGF), and by serum and non-serum stimulated transforming growth factor (TGF-α). In all cases 10 ml of growth factor was administered at a concentration of 1 ng/ml. Compound 47a was found to be consistently effective in reversing the growth of both cell lines. The reversal values are summarized in Table 6.

TABLE 6

$LC_{50}$ Data for Administered Drug

| Cell Line | Growth Factor | Serum Stimulated | Non-Serum Stimulated |
|---|---|---|---|
| MCF-7 | EGF | 1 μM | 5 μM |
|  | TGF | 5 μM | 50 μM |
| MDA-MB435 | EGF | 5 Mm | 7 mM |
|  | TGF | 1 μM | 2 μM |

Based on these preliminary results, the data indicated that a group of novel chalcone-like compounds were synthesized that exhibited a broad range of anti-cancer activity with significant reductions in cell viabilities against both human breast cancer cell lines MCF-7 and MDA-MB435. Only compounds (47a-e) were found to be active against the above cell lines. These agents were found to be as potent, and in some cases, more potent than known anti-breast cancer agents. These compounds exhibited the ability to reverse the stimulatory effects of known tyrosine kinases EGF and TGF α. This suggests that (47a-e) compounds might be exerting their anti-cancer effects against MCF-7 and MDA-MB435 cells by blocking the growth stimulatory effects of EGF and/or TGF α. These results indicate the importance of structural modifications of chemically similar drugs towards improving the efficiency and potency of potential antineoplastic agents.

Genistein's effects on cells, including inhibition of proliferation, induction of differentiation, apoptosis, and arrest of cells at cell cycle checkpoints are reminiscent of those of TGFβ1. This peptide growth factor was identified as a major factor that regulates eukaryotic cell proliferation by attenuating passage through cell cycle check-points. Exposure to genistein caused either synthesis and secretion of TGFβ1 by the HME cells or secretion of the preexisting intracellular pool of TGFβ1. The growth inhibitory effects of tamoxifen were nearly identical to those of genistein involving TGFβ1 on the growth of human breast cancer MCF-7 cells. For both compounds, the inhibition of cell proliferation was correlated with increased amounts of TGFβ1 in the culture medium and was blocked by antibodies against TGFβ1 added exogenously to the culture medium.

Humans, and other animals, in particular, mammals, suffering from breast cancer or other proliferative disorders can be treated by administering to the patient an effective amount of one or more of the above-identified compounds or a pharmaceutically acceptable salt or derivative or salt thereof in a pharmaceutically acceptable carrier or diluent. The active materials can be administered by any appropriate route, for example, orally, parenterally, intravenously, intradermally, or subcutaneously.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.5 to 500 mg/kg, preferably 1 to 100 mg/kg per day. The effective dosage range of the pharmaceutically acceptable salt or derivatives can be calculated based on the weight of the parent compound to be delivered. If the derivative exhibits activity in itself, the effective dosage can be estimated as above using the weight of the derivative, or by other means known to those skilled in the art.

The compound is conveniently administered in any suitable unit dosage form, including but not limited to one containing 1 to 3000 mg, preferably 5 to 500 mg of active ingredient per unit dosage form. An oral dosage of 25-250 mg is usually convenient.

The active ingredient should be administered to achieve peak plasma concentrations of the active compound of about 0.1 to 100 μM, preferably about 1-10 μM. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed invention. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salt or derivatives or salts thereof can also be administered with other active materials that do not impair the desired action, or with materials that supplement the desired action, such as other antiproliferative agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

Combination Therapy

Compounds of the present invention may be administered in combination with other anti-proliferative agents. When a combination of two or more anti-proliferative or potentially anti-proliferative agents is assayed, the results may indicate less inhibition of proliferation than what would be expected if the effects of the individual agents were additive, or the effects may represent the mathematical product of the expected effects of the two agents (additive inhibition). Alternatively, the inhibition actually observed experimentally may be greater than what would be expected as a simple product of the effects of the two agents. Such synergistic anti-tumor or antiproliferative effect is highly desirable. This synergistic effect of the compounds with other chemotherapeutic agents in the treatment of tumors, and especially of breast cancer, is contemplated by the present invention.

The chemotherapeutic agents used in combination with the compounds of the present invention include tamoxifen, toremifene, idoxifene, droloxifene, TAT-59, LY117018, raloxifene, genistein, doxyrubicin, Taxol, Taxotere, aredia, arimidex, navilbine, busulfan, cisplatin, cyclophosphamide (Cytoxan), dacarbazine, ifosfamide, interferon, mechlorethamine (Mustargen), melphalan, carmustine, lomustine, 5-fluorouracil, methotrexate, gemcitabine, cytarabine (Ara-C), fludarabine, bleomycin, dactinomycin, daunorubicin, idarubicin, paclitaxel, docetaxel, etoposide, vinblastine, vincristine, vinorelbine, prednisone, dexamethasone, and herceptin.

Whereas this invention has been described in detail with particular reference to its most preferred embodiments, it is understood that variations and modifications can be effected within the spirit and scope of the invention, as described herein before and as defined in the appended claims. The corresponding structures, materials, acts, and equivalents of all means plus function elements, if any, in the claims below are intended to include any structure, material, or acts for performing the functions in combination with other claimed elements as specifically claimed.

What is claimed is:

1. A compound of the formula:

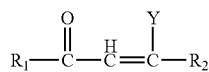

wherein:
R1 is adamantyl;
R2 is phenyl substituted by X;
wherein X is straight chain or branched C1-6 alkyl, amino, C1-6 alkyl amino, pyrrolidinyl, piperadinyl, morpholinyl, piperazinyl, C1-6 aralkoxyl, aryl, C1-6 aralkyl, cyano or a phosphorus containing group; and
Y is H;
or a pharmaceutically acceptable salt or derivative thereof.

2. A compound according to claim 1, having the formula

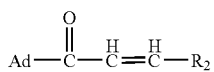

wherein
Y is hydrogen;
R2 is phenyl substituted by cyano, C1-4 alkyl, benzyloxy, and phenyl;
or a pharmaceutically acceptable salt or derivative thereof.

3. A compound according to claim 1, having the formula

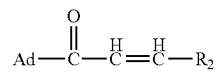

wherein
R2 is phenyl substituted by p-cyano, p-isopropyl, p-benzyloxy, p-phenyl, p-ethyl;
or a pharmaceutically acceptable salt or derivative thereof.

4. A pharmaceutical composition comprising an anti-proliferative effective amount of a compound of claim 1 having the formula

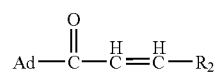

wherein
R2 is phenyl substituted by cyano, C1-4 alkyl, benzyloxy, and phenyl; or a pharmaceutically acceptable salt or derivative thereof, in combination with a pharmaceutically acceptable carrier.

5. A pharmaceutical composition comprising an anti-proliferative effective amount of a compound of claim 1 having the formula

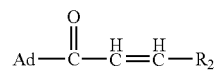

wherein
R2 is phenyl substituted by p-cyano, p-isopropyl, p-benzyloxy, p-phenyl, p-ethyl;
or a pharmaceutically acceptable salt or derivative thereof in combination with a pharmaceutically acceptable carrier.

6. A pharmaceutical composition comprising an anti-proliferative effective amount of a compound of claim 1, in combination with a pharmaceutically acceptable carrier.

* * * * *